United States Patent
Pedro

(10) Patent No.: US 11,056,233 B2
(45) Date of Patent: Jul. 6, 2021

(54) CONTROLLER-BASED APPARATUS AND METHOD FOR DIAGNOSIS AND TREATMENT OF ACQUIRED BRAIN INJURY AND DYSFUNCTION

(71) Applicant: Victor M. Pedro, East Greenwich, RI (US)

(72) Inventor: Victor M. Pedro, East Greenwich, RI (US)

( * ) Notice: Subject to any disclaimer, the term of this patent is extended or adjusted under 35 U.S.C. 154(b) by 485 days.

(21) Appl. No.: 15/584,695

(22) Filed: May 2, 2017

(65) Prior Publication Data
US 2017/0231515 A1 Aug. 17, 2017

Related U.S. Application Data

(63) Continuation-in-part of application No. 14/284,864, filed on May 22, 2014, which is a continuation of
(Continued)

(51) Int. Cl.
*A61B 5/00* (2006.01)
*A61B 5/11* (2006.01)
(Continued)

(52) U.S. Cl.
CPC .......... *G16H 40/67* (2018.01); *A61B 5/0006* (2013.01); *A61B 5/0205* (2013.01);
(Continued)

(58) Field of Classification Search
CPC ......... A61B 5/0205; A61B 5/103; A61B 5/11; A61B 5/4035; A61B 5/4076; A61B 5/4082; A61B 5/4266; A61B 5/4884
(Continued)

(56) References Cited

U.S. PATENT DOCUMENTS 5,267,942 A 12/1993 Saperston
5,299,119 A 3/1994 Kraf et al.
(Continued)

OTHER PUBLICATIONS

Chang et al., "Chiropractic Neurology: Breakthrough Treatment or Placebo?" http://abcnews.go.com/Health/chiropractic-neurology-breakthrough-placebo/story?id=17027630&singlePage=true, 2 pages, Aug. 17, 2012.
(Continued)

*Primary Examiner* — Nathan J Jenness
(74) *Attorney, Agent, or Firm* — Sunstein LLP

(57) ABSTRACT

A controller-based apparatus for diagnosis and treatment of a subject with acquired brain injury and dysfunction. Various embodiments of the invention described herein recognize that different body postures affect the autonomic nervous system differently, and therefore various external stimuli may have different therapeutic efficacies when a patient or subject is in each body posture. Postures, such as walking, sitting, standing, prone and supine, have different effects on the autonomic nervous system, and therefore some stimuli have different physiological efficacies while a patient or subject is in a given body posture. Disclosed embodiments of the present invention leverage this relationship to provide a controller-based apparatus that determines a combination of posture and stimulus that has optimal therapeutic effect, while minimizing health practitioner involvement. The controller based apparatus provides a treatment that stimulates the nervous system through a combination of noninvasive therapies that stimulate brain cells to increase their efficiency—this promotes the formation of pathways that help transfer information throughout the brain in such a way that in the end, the affected area of the brain and overall brain function are improved without medication or surgery.

15 Claims, 8 Drawing Sheets

Related U.S. Application Data application No. 14/033,004, filed on Sep. 20, 2013, now Pat. No. 10,888,274.

(60) Provisional application No. 61/726,511, filed on Nov. 14, 2012.

(51) Int. Cl.

| | |
|---|---|
| *A61B 5/0205* | (2006.01) |
| *A61B 5/24* | (2021.01) |
| *G16H 40/67* | (2018.01) |
| *A61B 5/1455* | (2006.01) |
| *G16H 20/40* | (2018.01) |
| *A61B 3/113* | (2006.01) |
| *A61B 3/11* | (2006.01) |

(52) U.S. Cl.
CPC ........... *A61B 5/1116* (2013.01); *A61B 5/1118* (2013.01); *A61B 5/14551* (2013.01); *A61B 5/24* (2021.01); *A61B 5/4035* (2013.01); *A61B 5/4058* (2013.01); *A61B 5/4076* (2013.01); *A61B 5/4266* (2013.01); *A61B 5/4884* (2013.01); *G16H 20/40* (2018.01); *A61B 3/112* (2013.01); *A61B 3/113* (2013.01); *A61B 5/02055* (2013.01); *A61B 5/1104* (2013.01); *A61B 5/1126* (2013.01); *A61B 5/4848* (2013.01); *Y02A 90/10* (2018.01)

(58) Field of Classification Search
USPC ........................... 600/300–301; 128/897–898
See application file for complete search history.

(56) References Cited

U.S. PATENT DOCUMENTS

| | | | | |
|---|---|---|---|---|
| 6,007,459 | A | 12/1999 | Burgess | |
| 6,685,729 | B2 | 2/2004 | Gonzalez | |
| 2002/0045835 | A1* | 4/2002 | Masakov | A61B 5/0205 |
| | | | | 600/481 |
| 2004/6685729 | | 2/2004 | Gonzalez | |
| 2004/0158297 | A1 | 8/2004 | Gonzalez | |
| 2005/0056290 | A1 | 3/2005 | Feinberg | |
| 2007/0161912 | A1 | 7/2007 | Zhang et al. | |
| 2008/0171923 | A1 | 7/2008 | Bolea et al. | |
| 2009/0312849 | A1* | 12/2009 | Cosgrove | H04S 7/303 |
| | | | | 700/28 |
| 2010/0240945 | A1* | 9/2010 | Bikko | A61B 5/02405 |
| | | | | 600/28 |
| 2013/0184603 | A1* | 7/2013 | Rothman | A61B 5/7264 |
| | | | | 600/544 |
| 2014/0135590 | A1 | 5/2014 | Pedro | |
| 2014/0330093 | A1* | 11/2014 | Pedro | A61B 5/0205 |
| | | | | 600/301 |

OTHER PUBLICATIONS

Damasio, "Looking for Spinoza: Joy, Sorrow, and the Feeling Brain," A Harvest Book, Harcourt, Inc., 2003.
Damasio, "Descartes' Error: Emotion, Reason, and the Human Brain," Penguin, 2005.
Damasio et al., "Minding the Body," Daedalus, vol. 135, No. 3, pp. 15-22, 2006.
Fleuren et al., "Influence of Posture and Muscle Length on Stretch Reflex Activity in Poststroke Patients With Spasticity," Arch. Phys. Med. Rehabil., vol. 87, pp. 981-988, Jul. 2006.
Gao et al., "Brain-Modulated Effects of Auricular Acupressure on the Regulation of Autonomic Function in Healthy Volunteers," Evidenced-Based Complementary and Alternative Medicine, vol. 2012, Article ID 714391, 8 pages, Jun. 11, 2011.
Gulli, "Rebuilding Sidney Crosby's brain," Maclean's, http://www.macleans.ca/society/rebuilding-crosbys-brain/, 10 pages, Nov. 3, 2011.
Jones, "Thalamocortical dysrhythmia and chronic pain," Pain (Elsevier) 150: 4-5, 2010.
Leigh et al., "Neuroscience of Eye Movements," published by ACNR, vol. 5, No. 6, pp. 12, 13-15, Jan./Feb. 2006.
Leigh et al., "The Neurology of Eye Movements," Contemporary Neurology Series, New York: Oxford University Press, 4th Edition, Apr. 2006.
Llinás et al., "The Mind-Brain Continuum: Sensory Processes," A Bradford Book, The MIT Press, 1996.
Llinás, et al., "The neuronal basis for consciousness," Phil. Tran. R. Soc. Lond. B (The Royal Society), vol. 353, No. 1377, pp. 1841-1849, Nov. 1998.
Llinás, et al., "Thalamocortical dysrhythmia: A neurological and neuropsychiatric syndrome characterized by magnetoencephalography," PNAS, vol. 96, No. 26, pp. 15222-15227, Dec. 1999.
Llinás, "I of the Vortex: From Neurons to Self," A Bradford Book, The MIT Press, 2001.
Llinás, "Temporal binding via cortical coincidence detection of specific and nonspecific thalamocortical inputs: A voltage-dependent dye-imaging study in mouse brain slices," PNAS (The National Academy of Sciences) vol. 99, No. 1, pp. 449-454, 2002.
Yokota et al., "Motion sickness susceptibility associated with visually induced postural instability and cardiac autonomic responses in healthy subjects," Acta Oto-Laryngologica, pp. 280-285, 2005.
United States Patent and Trademark Office, Office Action dated May 25, 2017 pertaining to U.S. Appl. No. 14/033,004, 12 pages.
United States Patent and Trademark Office, Office Action dated Jun. 21, 2017 pertaining to U.S. Appl. No. 14/284,864, 11 pages.

* cited by examiner

CONTROLLER-BASED APPARATUS AND METHOD FOR DIAGNOSIS AND TREATMENT OF ACQUIRED BRAIN INJURY AND DYSFUNCTION

CROSS-REFERENCE TO RELATED APPLICATIONS

This application is a continuation-in-part of U.S. application Ser. No. 14/284,864, filed May 22, 2014, which in turn is a continuation of U.S. application Ser. No. 14/033,004, filed Sep. 20, 2013, which in turn claims the benefit of U.S. Provisional Application 61/726,511, filed Nov. 14, 2012. Each of these above-described applications is hereby incorporated herein by reference in its entirety.

TECHNICAL FIELD

The present invention relates to a controller-based apparatus for diagnosis and treatment of a subject with acquired brain injury and dysfunction.

BACKGROUND ART

It is known in the prior art that acquired brain injury and dysfunction is one the leading causes of disability. Such injury and dysfunction not only includes traumatic brain injury, but also encompasses conditions and illnesses of the brain and central nervous system which are not necessarily due to blunt trauma, for example: genetics, learning disabilities, reflex sympathetic dystrophy (RSD) syndrome, complex regional pain syndrome (CRPS), tremors, and dystonia. More particularly, in addition to the obvious, highly visible victims—returning soldiers and those who have suffered strokes—it is reported that a very high percentage of today's prison inmates have some form of brain injury related impairment. The advanced training and methods of first responders and emergency departments has led to a much greater rate of surviving a major traumatic head/brain injury. Adding to this population are children and young adults who have suffered sports related head injuries, as well as violence/abuse related brain injury. Another population affected by brain injury/dysfunction is those with developmental disorders and learning disabilities. Whether the etiology of this dysfunction is genetic, congenital or environmental, it still manifests an underlying brain function anomaly. These disorders can be comorbid with traumatically acquired brain injury and therefore greatly compound the overall impairment. Many of these injuries result in lasting changes in memory, computational, emotional, as well as autonomic function. It is reported that unemployment among this population is disproportionately high, and some find it impossible to maintain employment, even with placement, due to their cognitive impairments.

The diagnosis and treatment of brain-based lesions have been extremely dependent upon the geographic location and the particular facility within that location where treatment is sought. The choice of intervention and which treatment protocols that are followed are based largely upon the traditions and practices of the particular therapists and doctors who compose the patient's treatment team. Frequently in these cases, only the life threatening aspects of the disorder/injury are addressed, neglecting soft or 'functional/physiological' lesions, even if an extensive rehabilitation regimen is undertaken. It is a widely held belief in social work, cognitive rehabilitation, and nutritional counseling that once stabilization has occurred following post-neuro-surgical, traumatic, acquired brain injury, therapy directed at producing lasting change to the structural and functional integration should be a major portion of any rehabilitation process.

Moreover, there is a functional and spatial mapping between different areas of the brain and different areas of the body. For example, the body includes afferent nerves that carry sensory signals to the central nervous system, including the state of smooth muscle contraction in arteries, the amount of local blood flow to an area, local temperature, the presence of chemistry related to tissue injury, and pH, $O_2$, and $CO_2$ levels. By contrast, efferent nerves carry motor signals from the central nervous system to the muscles. These two types of nerves serve different purposes, and are located in different places within the brain. Injuries to different parts of the brain therefore sometimes manifest themselves as dysfunction of different areas of the body, either as diminished sensory capability or as diminished motor capability.

Small diameter afferent fibers consist of Type C and A$\delta$ peripheral nerve fibers. These are thin, unmyelinated, and slow conducting in nature. The information they relay includes the state of smooth muscle contraction in arteries, the amount of local blood flow to an area, local temperature, the presence of chemistry related to tissue injury, and pH, $O_2$, and $CO_2$ levels. Type 2 C fibers are strongly activated by non-painful cold and heat stimulation. These fibers converge onto the VMpo thalamic nucleus, and by way of the NTS and PB (Parabrachial) nucleus, onto the VMb thalamic nucleus. The VMpo thalamic nucleus fibers connect onto the anterior and posterior insular neural maps. Fibers from the VMb thalamic nucleus synapse onto the posterior insular cortex.

Using traditional treatment methods for chronic pain have had poor outcomes, especially if the pain is caused by a sympathetic nervous system disorder that can be exacerbated by a wide variety of unrelated triggers such as food and weather. Some individuals may simply cope with the pain, traveling from doctor to doctor, never getting an accurate diagnosis, being told that their pain is "all in their head". One such disorder is reflex sympathetic dystrophy (RSD) syndrome, also known as complex regional pain syndrome (CRPS). RSD has no known cause and no known cure.

Furthermore, traditional treatment methods are often time consuming and complicated for both the patient and the doctor. This can result in increased costs for the patient.

SUMMARY OF THE EMBODIMENTS

Various embodiments of the invention described herein recognize that different body postures affect the autonomic nervous system differently, and therefore various external stimuli may have different therapeutic efficacies when a patient or subject is in each body posture. Postures, such as walking, sitting, standing, prone and supine, have different effects on the autonomic nervous system, and therefore some stimuli have different physiological efficacies while a patient or subject is in a given body posture. Disclosed embodiments of the present invention leverage this relationship to provide a controller-based apparatus that determines a combination of posture and stimulus that has optimal therapeutic effect, while minimizing health practitioner involvement. These controller based apparatus provides a treatment that stimulates the nervous system through a combination of noninvasive therapies that stimulate brain cells to increase their efficiency—this promotes the formation of pathways that help transfer information throughout the brain in such a way that in the end, the affected area of the brain and overall brain function are improved without medication or surgery. Indeed, the autonomic response advantageously may be addressed as the first step in the examination and rehabilitation process. It is further noted that, while the controller-based apparatus provides a treatment that may alleviate some symptoms of an underlying disability or illness, such as complex regional pain or RSD, it might not cure all the causes of the illness. Further embodiments thus provide for reevaluating the optimality of the posture/stimulus combination once relative normalcy has been achieved with respect to a given monitored physiological response, to determine whether any residual dysregulation remains.

In accordance with an embodiment of the invention, a controller-based apparatus is provided for diagnosis and treatment of a subject with acquired brain injury and dysfunction, by stimulation of afferent fibers so as indirectly to cause improvement in the area of the brain affected by the injury, and in overall brain function. A controller is configured to execute a diagnostic and treatment program, used to perform a protocol for the diagnosis and the treatment, the program operating under guidance of a health practitioner. A display is coupled to the controller, configured to provide data to the health practitioner concerning performance of the subject under the protocol as well as a user interface for the health practitioner as to operation of the diagnostic and treatment program. A stimulus array is coupled to the controller. The stimulus array is configured to provide stimulation to the subject, the stimulation being provided from a stimulus set selected from TENS, non-painful heat, non-painful cold, visual, occulo-motor stimulation, crude touch, olfactory stimulation, vestibular stimulation, auditory stimulation and combinations thereof. A sensor array is coupled to the controller. The sensor array is configured to monitor a response set of autonomic physiological responses of the subject, to such stimulation, the response set selected from oxygen saturation, heart rate, pupillary response, blood pressure, sweat production, sudomotor activity, and respiration. The protocol includes diagnostic processes including: providing by the controller, under control of the program, directions to the subject to assume sequentially a plurality of distinct postures in a posture set selected from the group consisting of walking, standing, sitting, prone and supine; while the subject is in each of the selected postures, using the stimulus array, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation; storing, under control of the program, diagnostic response data characterizing the responses of the subject to such diagnostic stimulation; retrieving, under control of the program, the diagnostic response data; processing, under control of the program, the diagnostic response data to identify the posture, hereinafter the "primary posture," wherein the physiological responses of the subject exhibit a least amount of dysfunction relative to their corresponding statistical norms; processing, under control of the program, the diagnostic response data identifying the stimulus, hereinafter the "primary stimulus," with respect to which the physiological responses of the subject exhibit a change in the amount of dysfunction towards their corresponding statistical norms when the subject is in the primary posture. The protocol further includes treatment processes including: (i) providing by the controller, under control of the program, direction to the subject to assume the primary posture; (ii) while the subject is in the primary posture, using the stimulus array, under control of the program, to provide treatment stimulation to the subject by the primary stimulus in the stimulus set while using the sensor array, under control of the program, to monitor the set of autonomic physiological responses of the subject to the treatment stimulation; (iii) storing, under control of the program, treatment response data characterizing the responses of the subject to the treatment stimulation; (iv) under control of the program, retrieving and processing the treatment response data to determine if the treatment response data show achievement by the subject of a desired endpoint physiological condition, for the primary posture and the primary stimulus, in which the physiological responses to the identified stimulus approach a state of normalcy relative to their corresponding statistical norms and if not, then, under control of the program, repeating processes (i), (ii), (iii), and (iv). The protocol promotes thalamocortical pathways within the brain.

In accordance with related embodiments of the invention, the protocol may include further treatment processes. If the treatment response data show achievement by the subject of a desired endpoint physiological condition, for the primary posture and the primary stimulus, then under control of the program: (v) the controller provides, under control of the program, direction to the subject to assume a posture, hereinafter the "secondary posture," in the posture set other than the primary posture; vi) while the subject is in the secondary posture, the stimulus array is used, under control of the program, to provide treatment stimulation to the subject by a selected stimulus in the stimulus set, hereinafter the "secondary stimulus," while using the sensor array, under control of the program, to monitor the set of autonomic physiological responses of the subject to the treatment stimulation in the secondary posture; (vii) storing, under control of the program, secondary posture treatment response data characterizing the responses of the subject to the treatment stimulation in the secondary posture; (viii) under control of the program, retrieving and processing the secondary posture treatment response data to determine if the secondary posture treatment response data show a further desired endpoint physiological condition is achieved in which the physiological responses to the secondary stimulus at the secondary posture approach a state of normalcy relative to a their corresponding statistical norms; and (ix) if not, then, under control of the program, repeating processes (v), (vi), (vii), and (viii), and otherwise terminating the treatment process.

In accordance with further embodiments of the invention, the protocol may further include diagnostic processes including, while the subject is in the secondary posture, using the stimulus array, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation. Under control of the program, diagnostic response data characterizing the responses of the subject to such diagnostic stimulation is stored. Under control of the program, the diagnostic response data is retrieved. Under control of the program, processing the diagnostic response data to identify the secondary stimulus with respect to which the physiological responses of the subject exhibit a change in the amount of dysfunction towards their corresponding statistical norms when the subject is in the secondary posture.

In yet further embodiments of the invention, the acquired brain injury and dysfunction may include post-concussion syndrome (PCS). The acquired brain injury and dysfunction may be associated with at least one symptom, such as headaches, dizziness, neck pain, stiff neck, nervousness, fatigue, irritability, cold sweats, excessive eye sensitivity to light and combinations thereof, the protocol resulting in a decrease in the at least one symptom. The display may be coupled to an articulated swing-arm. The controller, under control of the program, may control the articulated swing-arm to assume various positions and/or orientations. The controller-based apparatus may include a speaker, a microphone and/or a headphone, functionally coupled to the controller. The controller-based apparatus may include a video headset configured to be worn by the subject, and wherein the controller, under control of the program, provides and/or receives visual information to and/or from the subject via the video headset, respectively.

In accordance with another embodiment of the invention, a non-transitory storage medium, encoded with instructions for a diagnostic and treatment program, is provided. The program, when executed on a system having a controller, a display, a stimulus array, and a sensor array, establishes processes for performing a protocol for the diagnosis and the treatment of a subject with acquired brain injury, by stimulation of afferent fibers so as indirectly to cause improvement in the area of the brain affected by the injury, and in overall brain function. The program operates under guidance of a health practitioner. The display is coupled to the controller and is configured by the program to provide data to the health practitioner concerning performance of the subject under the protocol as well as a user interface for the health practitioner to operate the diagnostic and treatment program. The stimulus array is coupled to the controller and configured by the program to provide stimulation to the subject. The stimulation is provided from a stimulus set selected from the group consisting of TENS, non-painful heat, non-painful cold, visual, occulo-motor stimulation, crude touch, olfactory stimulation, vestibular stimulation, auditory stimulation and combinations thereof. The sensor array is coupled to the controller and is configured by the program to monitor a response set of autonomic physiological responses of the subject, to such stimulation, the response set selected from the group consisting of oxygen saturation, heart rate, pupillary response, blood pressure, sweat production, sudomotor activity, and respiration. The protocol includes diagnostic processes that include the following: under control of the program, the controller provides directions to the subject to assume sequentially a plurality of distinct postures in a posture set selected from the group consisting of walking, standing, sitting, prone and supine; while the subject is in each of the selected postures, the stimulus array is used, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation; under control of the program, diagnostic response data is stored characterizing the responses of the subject to such diagnostic stimulation; under control of the program, the diagnostic response data is retrieved; Under control of the program, the diagnostic response data is processed to identify the posture, hereinafter the "primary posture," wherein the physiological responses of the subject exhibit a least amount of dysfunction relative to their corresponding statistical norms; and under control of the program, the diagnostic response data is processed to identify the stimulus, hereinafter the "primary stimulus," with respect to which the physiological responses of the subject exhibit a change in the amount of dysfunction towards their corresponding statistical norms when the subject is in the primary posture. The protocol further includes treatment processes that include the following: (i) under control of the program, the controller provides direction to the subject to assume the primary posture; (ii) while the subject is in the primary posture, the stimulus array is used, under control of the program, to provide treatment stimulation to the subject by the primary stimulus in the stimulus set while using the sensor array, under control of the program, to monitor the set of autonomic physiological responses of the subject to the treatment stimulation; (iii) under control of the program, treatment response data characterizing the responses of the subject to the treatment stimulation is stored; and (iv) under control of the program, the treatment response data is retrieved and processed to determine if the treatment response data show achievement by the subject of a desired endpoint physiological condition, for the primary posture and the primary stimulus, in which the physiological responses to the identified stimulus approach a state of normalcy relative to their corresponding statistical norms and if not, then, under control of the program, repeating processes (i), (ii), (iii), and (iv). The protocol promotes thalamocortical pathways within the brain.

In accordance with related embodiments of the invention, under control of the program encoded on the non-transitory storage medium, the protocol may include, if the treatment response data show achievement by the subject of a desired endpoint physiological condition, for the primary posture and the primary stimulus: (v) providing by the controller, under control of the program, direction to the subject to assume a posture, hereinafter the "secondary posture," in the posture set other than the primary posture; (vi) while the subject is in the secondary posture, using the stimulus array, under control of the program, to provide treatment stimulation to the subject by a selected stimulus in the stimulus set, hereinafter the "secondary stimulus," while using the sensor array, under control of the program, to monitor the set of autonomic physiological responses of the subject to the treatment stimulation in the secondary posture; (vii) storing, under control of the program, secondary posture treatment response data characterizing the responses of the subject to the treatment stimulation in the secondary posture; (viii) under control of the program, retrieving and processing the secondary posture treatment response data to determine if the secondary posture treatment response data show a further desired endpoint physiological condition is achieved in which the physiological responses to the secondary stimulus at the secondary posture approach a state of normalcy relative to a their corresponding statistical norms; and (ix) if not, then, under control of the program, repeating processes (v), (vi), (vii), and (viii), and otherwise terminating the treatment process.

In further related embodiments of the invention, under control of the program encoded on the non-transitory storage medium, the protocol may further include diagnostic processes including: while the subject is in the secondary posture, using the stimulus array, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation; storing, under control of the program, diagnostic response data characterizing the responses of the subject to such diagnostic stimulation; retrieving, under control of the program, the diagnostic response data; processing, under control of the program, the diagnostic response data identifying the secondary stimulus with respect to which the physiological responses of the subject exhibit a change in the amount of dysfunction towards their corresponding statistical norms when the subject is in the secondary posture.

In accordance with yet further related embodiments of the invention, the acquired brain injury includes post-concussion syndrome (PCS). The acquired brain injury may be associated with at least one symptom selected from the group consisting of headaches, dizziness, neck pain, stiff neck, nervousness, fatigue, irritability, cold sweats, excessive eye sensitivity to light and combinations thereof, and wherein the protocol results in a decrease in the at least one symptom. The system may further include a video headset configured to be worn by the subject, and the controller, under control of the program, provides and/or receives visual information to and/or from the subject via the video headset, respectively.

BRIEF DESCRIPTION OF THE DRAWINGS

The foregoing features of embodiments will be more readily understood by reference to the following detailed description, taken with reference to the accompanying drawings, in which:

FIG. 6(*b*) shows a subject in a standing position using the display, in accordance with an embodiment of the invention. FIG. 6(*c*) shows a subject using the display in a prone position, in accordance with an embodiment of the invention;

DETAILED DESCRIPTION OF SPECIFIC EMBODIMENTS

Figure 1:
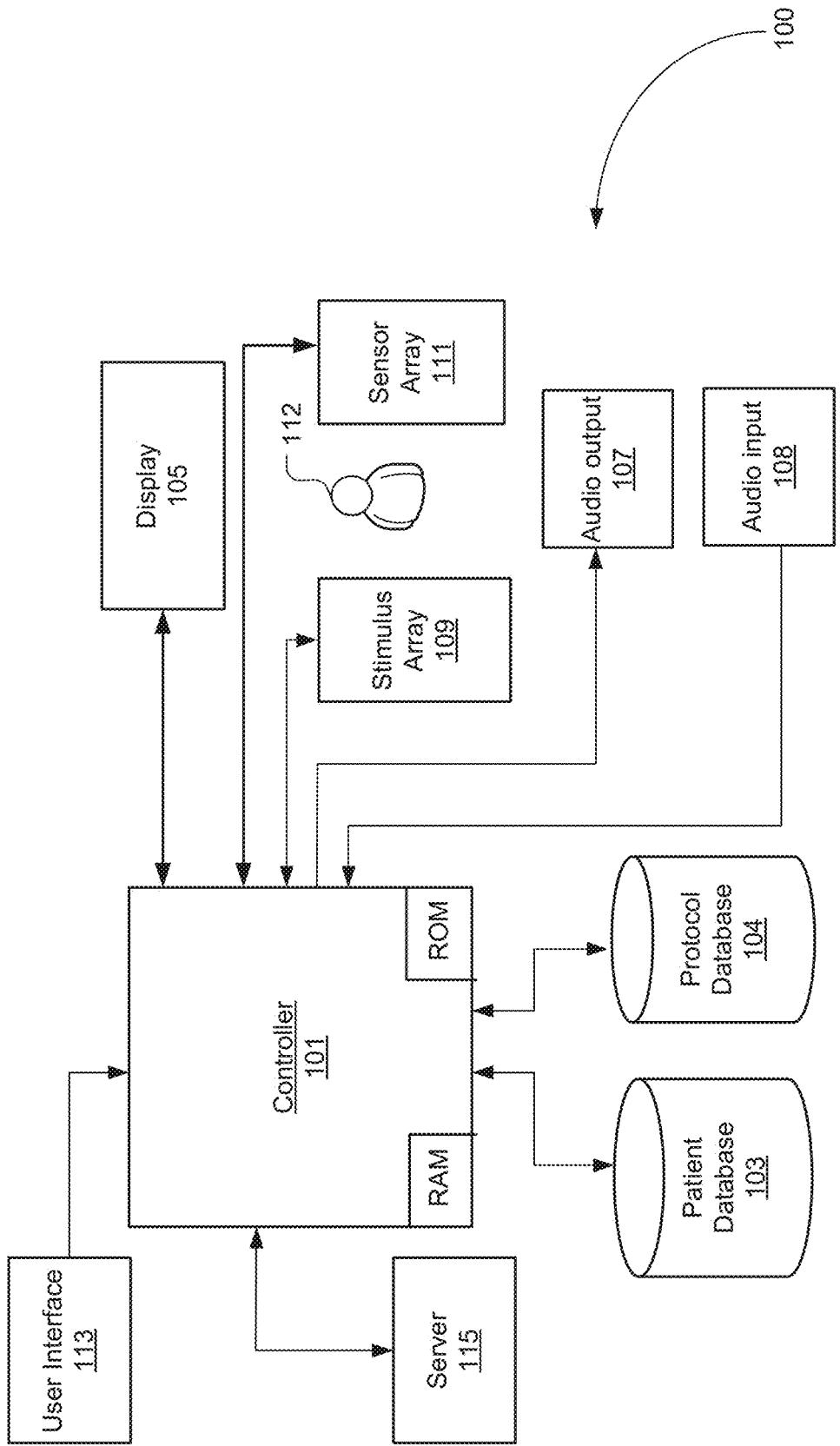
FIG. 1 is a block diagram of a controller-based apparatus, for diagnosis and treatment of a subject with acquired brain injury and dysfunction, in accordance with an embodiment of the invention.

In illustrative embodiments of the invention, a controller-based apparatus for diagnosis and treatment of a subject with acquired brain injury and dysfunction is presented. More particularly, the controller-based apparatus is configured to define and perform a protocol that, in part, stimulates afferent fibers so as indirectly promote thalamocortical pathways within the brain, resulting in improved brain function. The controller-based apparatus advantageously uses a sensor array and a stimulus array to perform the protocol in a highly precise, timely and efficient manner, with minimal supervision by the health practitioner. Details are provided below.

Various embodiments of the invention described herein produce lasting change by incorporating different combinations of posture and environmental stimuli into the controller-based apparatus's therapeutic protocol. Postures, such as walking, sitting, standing, prone and supine, have different effects on the autonomic nervous system, and therefore some stimuli have different physiological efficacies while a patient or subject is in each body position. Disclosed embodiments of the present invention leverage this relationship in a combination of posture and stimulus that has optimal therapeutic effect. These embodiments provide a controller-based treatment that stimulates the nervous system through a combination of noninvasive therapies that stimulate brain cells to increase their efficiency—which, as described above, promotes the formation of pathways that help transfer information throughout the brain in such a way that in the end, the affected area of the brain and overall brain function are improved without medication or surgery. Indeed, the autonomic response advantageously may be addressed as the first step in the examination and rehabilitation process.

The controller-based apparatus disclosed herein accurately and efficiently addresses one of the main problems inherent in injured or dysfunctional neurological tissue—that of fragility of the supporting structures, and insufficient ability to supply adequate fuel needed for the increased metabolic activity for repair of the damaged areas. This differs from prior approaches of non-emergent brain injury treatment which generally employed a strategy of doing nothing or of prescribing "rest".

As used in this description and the accompanying claims, the following terms shall have the meanings indicated, unless the context otherwise requires:

The "labyrinthine system" is the sensory system of the inner ear that contributes to movement and balance. It has two components: the semicircular canal system, which indicates rotational accelerations, and the otoliths, which indicate linear accelerations. The labyrinthine system signals to both the neural structures that control eye movements and to the muscles that control posture. The labyrinthine system is part of the vestibular system, whose primary purpose is to detect the motion of the head and then generate reflexes that stabilize gaze and maintain the body's posture in gravity.

The "vestibulo-ocular reflex" or "VOR" is a reflex eye movement that stabilizes images on the retina during head movement by producing an eye movement in a direction opposite to the head movement. Since slight head movement is present at all times, the vestibulo-ocular reflex is essential for stabilizing vision.

"Smooth pursuit" refers to eye movements made while closely following or tracking a moving target. By contrast, "saccades" are rapid, simultaneous movements of both eyes in the same direction that redirect the line of sight.

"Computerized tracking tests", as defined herein, are clinical tests that measure a patient's ability to match eye movements to visual target movements. Such clinical tests can be utilized to identify and diagnose disturbances in the central nervous system.

"Video electronystagmography", or "VENG" is a comprehensive evaluation of the occulo-motor and vestibular systems comprised of computerized tracking tests (smooth pursuits and saccades) and optokinetic nystagmus ("OKN"). The VENG evaluation can be used to detect involuntary movements of the eye caused by nystagmus. As part of the VENG evaluation, patients are typically fitted with lightweight goggles that house infrared cameras, which may be connected to the controller-based apparatus. The cameras track and record eye movements and pupillary responses to visual targets. When the test begins, patients may be directed by the controller-based apparatus to match their eye movements to those visual targets (i.e. lines, dots, etc.) that are projected onto a display screen in front of them. Tests typically range from 30-60 seconds, with varied target velocity, acceleration, and frequency. Throughout each test, the controller-based apparatus may measure the patient's overall accuracy and response time. For example, in some cases, the eye falls behind the target and has to make abrupt rapid movements to catch up (known as the "catch-up saccade"). At other times, the patient may be going faster than the target in anticipation of the next movement. Either response may reflect a disturbance in the central nervous system.

"Computerized dynamic posturography" or "CDP" is a non-invasive test of balance used to assess the central nervous system mechanisms involved in the control of posture and balance. Generally, CDP may be carried out by the controller-based apparatus by directing a patient to assume a standing posture on a fixed instrumented platform (force plate) with or without perturbing cushion. The platform is connected to sensitive detectors (force and movement transducers) that detect subtle oscillations of the body. Tests typically span 20 seconds with varied movements and head positions (i.e. neutral, left rotation, right rotation, flexion, extension, downward gaze). CDP produces metrics that identify minute spontaneous body sways and overall balance scores. Abnormalities or below-average scores may reflect impairments in the central nervous system ("CNS") that affect the posture control system.

A "caloric test" is a thermal test of the lateral semicircular canals that is used to identify disorders of the inner ear and/or to detect bilateral weakness of the brain. The standard bithermal caloric test may be performed on patients by irrigating warm and cold water into each ear sequentially. During the procedure, the patient is seated, with head inclined 30 degrees up from horizontal to ensure that the lateral canal is horizontal. Warm water is then slowly inserted into the ear canal on one side, using a large plastic syringe. The water is stopped after 30 seconds, and spontaneous nystagmus is observed. After a rest of approximately 5 minutes, the test is repeated on the other side. If no response is detected, the test is repeated using cold water.

Temperature change can be manipulated to stabilize a patient's autonomic functioning. In a typical "temperature test", the patient is directed by the controller based apparatus to lie horizontally on a bench. To dampen all forms of stimulation, the lights may darkened, with the patient wearing, for example, ear plugs and red tinted glasses. Varying heat and/or cold is then applied to the upper and lower extremities (specific side to be determined by the controller-based apparatus). This process trains the autonomic system to withstand environmental and physiological changes, thereby stimulating small diameter afferents to elicit autonomic responses.

"Chair rotation with visual fixation" is a test used to identify the presence of a central (cerebellar or brainstem) lesion. For this diagnostic test, the patient is seated upright in a rotating chair and directed by the controller-based apparatus to fix his/her eyes on a clearly visible target. Typically, the patient holds a pen in his/her hand and focuses his/her gaze on the tip of that pen. The patient is then spun slowly in either direction (to be determined by the computer-based apparatus based upon the cerebellar deficit) in quarter turns. Throughout this exercise, the adequacy of gaze holding is observed. Impaired gaze holding, or a drift of the eye in a certain direction, may indicate the presence of a lesion. Additionally, this exercise is utilized as a therapeutic modality to train the cerebellum and frontal lobe to suppress the nystagmus reflex that occurs during rotation.

"Transcutaneous electrical nerve stimulation" or "TENS" is a non-invasive, low-risk form of nerve excitation used to reduce acute and chronic pain and/or myospasm. A TENS unit is typically applied directly to the skin using two or more electrodes. The standard battery-operated TENS unit modulates pulse width, frequency, and/or intensity.

"Gait" means a manner of walking.

"Brain timing and sequencing" refers to a computerized evaluation that identifies the motoric system's processing speed in executing complex motor commands in response to a generated auditory or visual cue.

Temporal differences between the auditory cue and the patient's performance are measured in milliseconds, reflecting the patient's overall processing speed. To strengthen brain timing and sequencing, the complex motor commands—including hand and foot exercises—are repeated as therapeutic activities once treatment progresses.

"Stimulation" or "sensory stimulation" means any form of sensory modality that is used for diagnosis or treatment of a disease, and includes visual stimulation, auditory stimulation, occulo-motor stimulation, olfactory stimulation, vestibular stimulation, vibratory stimulation, caloric stimulation, temperature-change stimulation, TENS, non-painful heat, non-painful cold, and crude touch.

"Subject" or "patient" means an individual being treated for an illness.

"Illness" means an illness of a human being, and includes, among other things, migraine, reflex sympathetic dystrophy (RSD) syndrome or complex regional pain syndrome (CRPS), postural orthostatic tachycardia syndrome (POTS), concussion, traumatic brain injury (TBI), apraxia, apraxia of speech, aphasia, cervicogenic dizziness, migraine-associated vertigo, vestibular illnesses, attention deficit hyperactivity disorder (ADHD), autism, Asperger Syndrome, fibromyalgia, chronic fatigue, mal de débarquement syndrome (MdDS), multiple sclerosis (MS), Parkinson's disease, restless leg syndrome (RLS), insomnia, dysautonomias, peripheral nerve injuries, tremors, ataxia, asthma, and sciatica.

A summary of investigations into eye movements, their role in understanding brain function, and their use in diagnosis of neurological conditions can be found in a primer on visual neuroscience, entitled "Neuroscience of Eye Movements" by R. John Leigh, MD, FRCP and Sangeeta Khanna, MD, published by ACNR, VOLUME 5 NUMBER 6 JANUARY/FEBRUARY 2006. This paper as well as the book it references, Leigh R J, Zee D S, The Neurology of Eye Movements (Book/DVD), Fourth Edition, 4 ed. New York: Oxford University Press, 2006, are hereby incorporated herein by reference. In summary, this paper states that an understanding of normal eye movements and knowledge of their biological substrate, purpose and properties will greatly assist in determining the location of a neurological lesion. Dr. Leigh asserts that most diseases that affect the brain have, to some degree, an effect on eye movements.

FIG. 1 is a block diagram of a controller-based apparatus 100 for use in treating a subject 112 with acquired brain injury and dysfunction, in accordance with an embodiment of the invention. The acquired brain injury and dysfunction may be associated with a wide variety of brain injuries and illnesses such as, without limitation, traumatic brain injury, genetics, learning disabilities, reflex sympathetic dystrophy (RSD) syndrome, complex regional pain syndrome (CRPS), tremors, dystonia, post-concussion syndrome (PCS), a stroke, a sports injury, a military related injury, traffic accidents and violence/abuse related brain injuries.

The controller-based apparatus 100 includes a controller 101. The controller 101 is configured to execute, under the guidance of a health practitioner, a diagnostic and treatment program, used to perform a protocol for the diagnosis and treatment of a subject 112 with acquired brain injury and dysfunction. 10. The diagnostic and treatment program may be encoded on, without limitation, a non-transitory storage medium. For example, the diagnostic and treatment program may be stored in the protocol database on a non-transitory storage medium, as described below.

The controller 101 may include, without limitation, a microprocessor and/or other various digital and/or analog components known in the art. The controller 101 may include, for example, a processor executing or controlled by, instructions stored in a memory (such as a program in software). The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible, non-transitory, non-writable storage media (e.g., read-only memory devices within a computer, such as ROM, or devices readable by an I/O attachment, such as CD-ROM or DVD disks), information alterably stored on tangible, non-transitory, writable storage media (e.g., floppy disks, removable flash memory and hard drives) or information conveyed to the controller through a communication medium, including wired or wireless computer networks. Portions or all of the controller 101 may be implemented using various circuitry/hardware, such as combinatorial logic, Application Specific Integrated Circuits (ASICs), Field-Programmable Gate Arrays (FPGAs), and firmware, or combinations thereof.

One or more displays 105 or other user interfaces 113 may be coupled to the controller 101. The display 105 may be, without limitation, a touch display, an LCD display and/or a display controlled with a mouse or other point/click device. The display 105 may have an associated keyboard. In various embodiments, a display 105 may be used to interface with the subject 112 during either or both diagnosis and treatment. The same display 105, or a different display 105, may be used by a health practitioner to provide data to the health practitioner concerning performance of the subject under the protocol, and/or as a user interface for the health practitioner as to operation of the diagnostic and treatment program. The display 105 may be attached to an articulated swing-arm, as described below in connection with FIG. 6.

The controller-based apparatus may include other user interfaces 113, including, without limitation, various knobs, buttons, sliders and/or switches. Haptic devices that provide feedback during diagnostics and/or treatment may be used that allow the patient to have greater interaction with the controller. The haptic feedback may be provided by wired, wireless, remote controlled, bodily attached, pads, clips, bands, adhesive electrodes, mats, platforms, hand-held controllers, and/or integrated into existing sensors.

The controller 101 may be coupled to audio input 108 and/or audio output 107. The audio output 107 may include, without limitation, one or more speakers and/or headphones. Audio input 108 may include, without limitation, one or more microphones. The audio input 108 and/or audio output 107 may provide dedicated or shared audio input/output to either or both the health practitioner and/or subject 112. Audio output 107 to the subject may include, without limitation, detailed instructions and/or act as stimulus with regard to either or both diagnostics and treatment. Headphones may be provided with large, soft ear pads that cover over the subject's ears. The large pads allow for greater patient comfort, and to block out the greatest amount of ambient noise which is especially present in an inpatient setting. The controller 101 may employ the headphones using a tone generator for precision auditory testing-treatment stimulations.

The controller 101 may be coupled to a patient database 103 and/or a protocol database 104 via a hard-wired or wireless interface. The patient database 103 and/or a protocol database 104 may reside on memory which may be random access memory (RAM), read-only memory (ROM), flash memory or any other memory, or combination thereof, suitable for storing data. Portions, or all, of the database(s) 102 and 104 may be permanently stored on tangible, non-transitory, non-writable storage media (e.g., read-only memory devices within a computer, such as ROM, or devices readable by an I/O attachment, such as CD-ROM or DVD disks), information alterably stored on tangible, non-transitory, writable storage media (e.g., floppy disks, removable flash memory and hard drives) or information conveyed to the controller through a communication medium, including wired or wireless computer networks.

The patient database 103 may be used to store and/or retrieve data associated with a plurality of patients, including the subject 112. The patient database 103 may be used to store all relevant data regarding the subject(s) 112, including the case history of the subject(s) 112, previous physical examinations, laboratory and treatment results, notes or logs related to the subject 112, medications prescribed, diagnoses and/or prognoses.

The protocol database 105 includes the various protocols that may be run by the controller 101 in diagnosing and treating the subject 112. The protocols may advantageously minimize the amount of time and energy needed by the health practitioner to perform the diagnosis and treatment, as the controller-based apparatus 100 may assume the major role in interfacing with the subject 112. Furthermore, the protocols may advantageously have the controller-based apparatus 100 perform evaluations/measurements that are impractical or impossible for the health practitioner to conduct.

Access to the controller 101, patient database 103 and/or the protocol database 105 may be password protected and require logging on and off. Identification may be required, and all security/Health Insurance Portability and Accountability Act (HIPAA) requirements may be met.

The controller 101 may also be coupled to a server 115 via a hardwired and/or wireless interface. Server 115 may connect, for example, with the Internet, allowing transfer of information to and from a limitless number of devices worldwide. In various embodiments, the server 115 may provide secure communications to a medical resource. Such communications may provide a secure community to share patient information and collaborate with medical colleagues, and may be, for example, HIPAA compliant.

The controller 101 may be further coupled, via a wired or wireless interface, to both a stimulus array 109 and a sensor array 111, in accordance with various embodiments of the invention.

The stimulus array 109 may be configured to provide stimulus to the subject 112 under control of the controller 101 program. The stimulus may include, without limitation, TENS, non-painful heat, non-painful cold, visual stimulation, occulo-motor stimulation, crude touch, olfactory stimulation, vestibular stimulation, or auditory stimulation and combinations thereof. The stimulus array 109 may include, without limitation: a TENS unit; Video electronystagmography (VENG) equipment; an ultrasound unit (e.g., for application of high frequency sound waves to deliver heat to particular areas of the subject); an electronic blanket/pad/mat, heating lamp; an ice/cold therapy unit; a hydronic temperature stimulator; a display; a virtual reality system; video display glasses or goggles; an olfactometer; a computerized dynamic posturography platform (e.g., a dynamic force plate with rotation and/or twist); rotating platforms/chairs; haptic technology that may be used to apply mechanical stimulation, forces, vibrations or motions to the subject; speakers; and other stimulators known in the art.

The sensor array 111 is configured to monitor autonomic physiological responses of the subject to provided stimulation. The sensor array 111 may measure, without limitation, oxygen saturation, heart rate, pupillary response, blood pressure, sweat production, sudomotor activity, temperature and/or respiration. The sensor array 11 may include, without limitation: pupillometry goggles, a pulse oximetry sensor; a respiratory sensor; a heart rate/pulse rate and/or blood pressure sensor; an electrocardiogram (EKG) unit; a pupilometer; a sweat sensor; a temperature sensor; a haptic sensor, a goniometer (e.g., that measures range of motion/joint angles of the body, which may be used for precise measurements of motions affecting specific semi-circular canals and otoliths during various diagnostics/treatment), an accelerometer; and/or other sensors known in the art.

Figure 2:
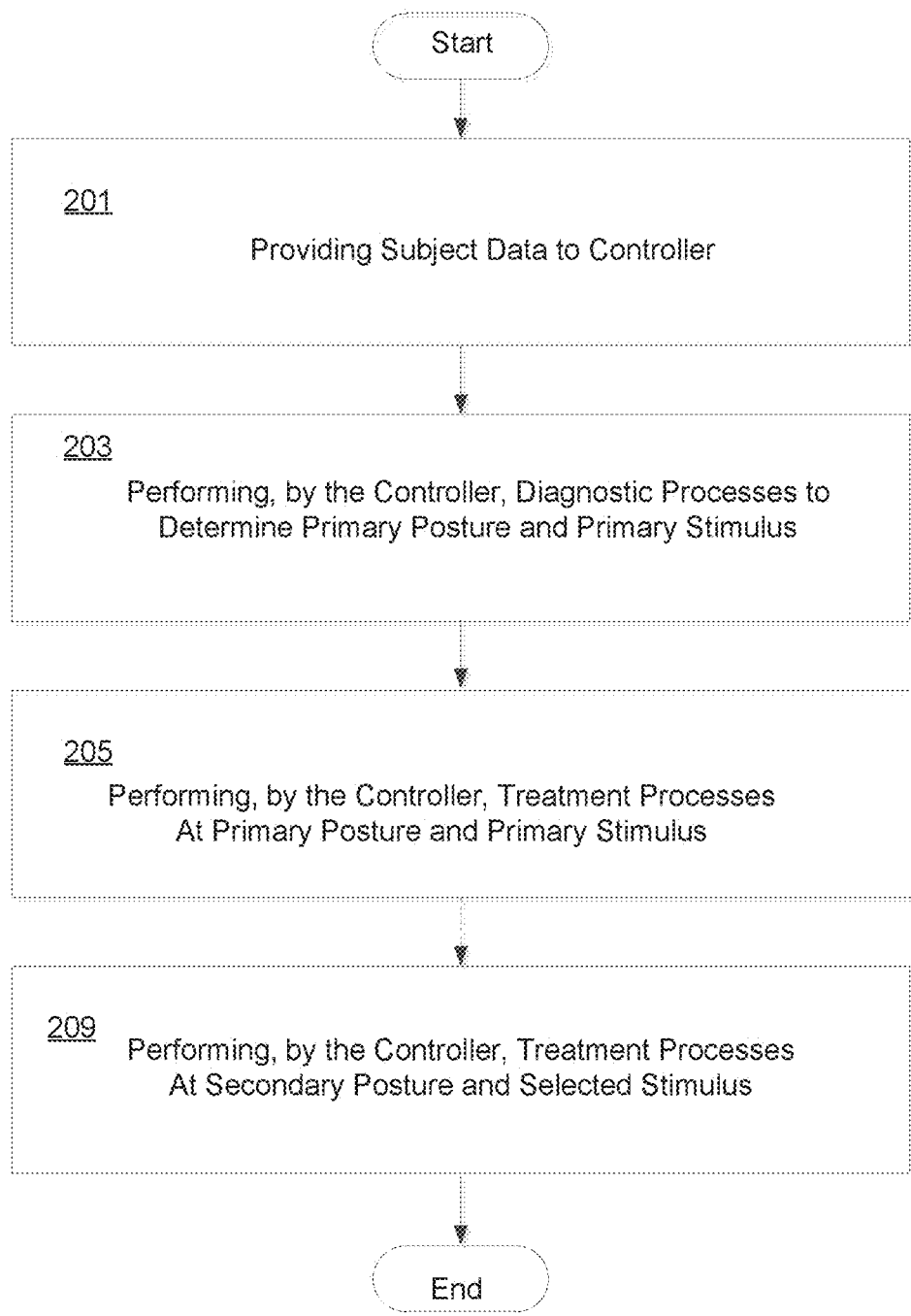
FIG. 2 shows a protocol for the diagnosis and treatment of a subject with acquired brain injury and dysfunction, in accordance with an embodiment of the invention.

FIG. 2 shows a protocol for the diagnosis and treatment of a subject with acquired brain injury and dysfunction, in accordance with an embodiment of the invention. The protocol may be performed by a controller-based apparatus executing a diagnostic and treatment program under control of the controller program, as described above. The program may operate under guidance of a health practitioner. For example, the health practitioner may, without limitation, enter subject data; initiate, select or interrupt the diagnosis and treatment; help the subject, when appropriate, to interface with the stimulus array and/or sensor array; and otherwise ensure that the diagnostics and treatment is running smoothly.

The protocol begins at step 201, in which subject data is provided to the controller. The subject data may be, without limitation, entered and/or selected via a user interface by the health practitioner and/or subject. In various embodiments of the invention, the controller provides an active role in acquiring the subject data. For example, the controller may query either the subject and/or the health practitioner visually via a display, and/or verbally via a speaker/microphone. Subject data may also be retrieved from a server (e.g., the internet). Any subject data provided to the controller may be saved to the patient database. In the event that the subject has already received previous treatment, the controller may query the patient database 103 to determine if data associated with the patient has already been entered into the patient database, and if so, retrieve and/or amend the subject data.

The subject data may include, for example, the identity of the patient, and any associated demographics, picture, video and/or audio. Furthermore, the subject data may include any pertinent information related to the injury and/or treatment, including, without limitation, the case history of the subject, previous physical examinations, Once the subject data has been provided, the controller performs diagnostic processes to determine a primary posture and a primary stimulus, at step 203. At the primary posture and using the primary stimulus, the controller then performs treatment processes, step 204. Afterwards, the controller may perform treatment processes at a secondary posture and selected stimulus, step 209. Each of these steps is described in more detail below. It should be noted that the diagnostics/treatment may be halted any time the provided stimulation caused negative changes in physiological responses.

Figure 3:
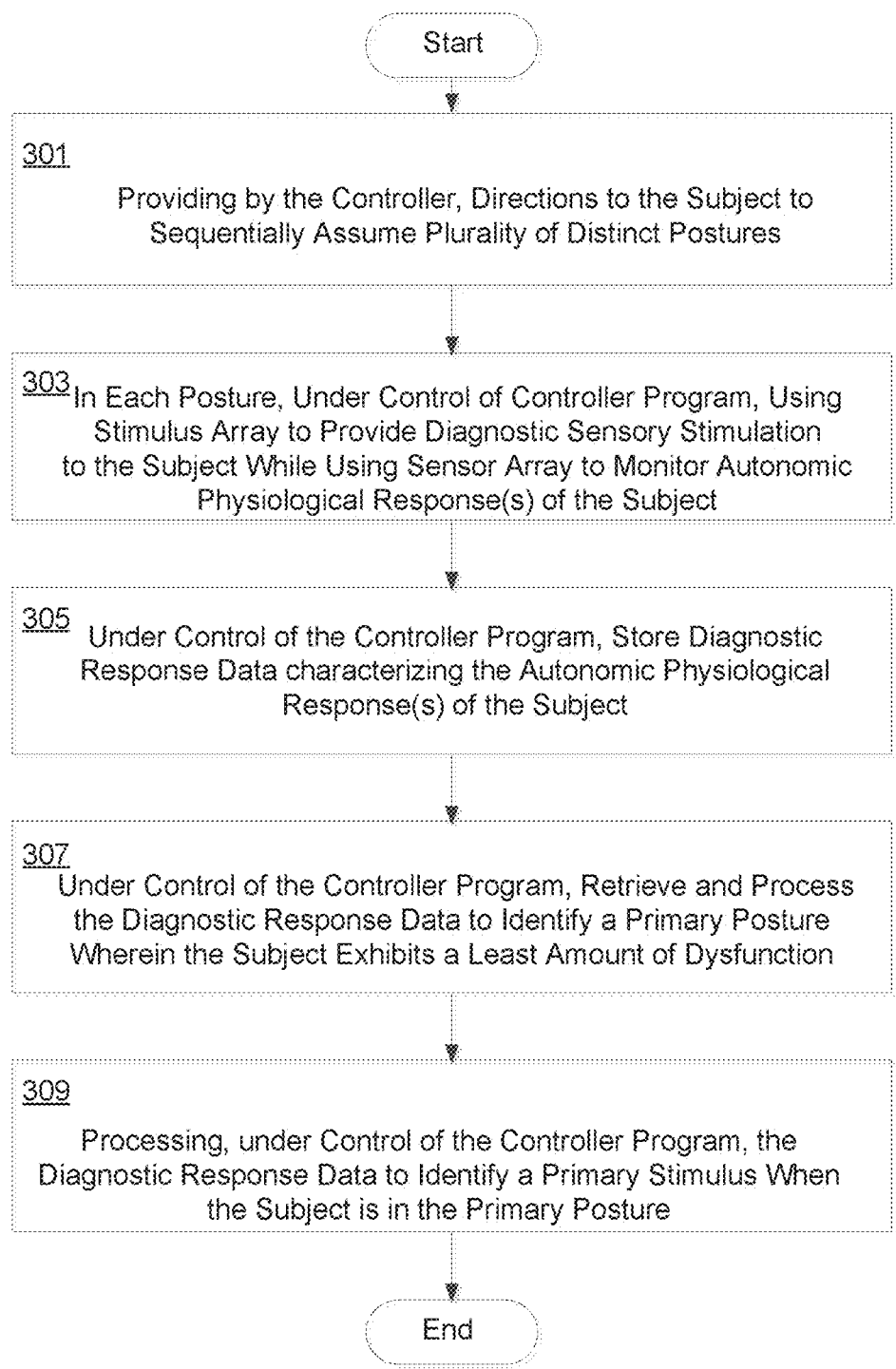
FIG. 3 shows a protocol for the diagnosis of a subject with acquired brain injury and dysfunction, in accordance with an embodiment of the invention.

FIG. 3 shows a diagnostic process that the controller may perform to determine a primary posture and a primary stimulus, in accordance with an embodiment of the invention. To start, the controller may provide directions to the subject to sequentially assume a plurality of distinct postures, step 301. The postures may include, without limitation, walking, standing, sitting, prone and supine. These directions may be provided by controller to the subject and/or health practitioner using, for example, a display or audio speaker.

In each of the selected postures, the stimulus array may then be used by the controller to provide to the subject sequentially each stimulus in a stimulus set so as to provide diagnostic stimulation, step 303. The stimulus set may include at least some of the following stimuli: TENS, non-painful heat, non-painful cold, visual, occulo-motor stimulation, crude touch, olfactory stimulation, vestibular stimulation and auditory stimulation. During the diagnostic stimulation, the controller uses the sensor array to monitor a set of autonomic physiological responses of the subject to the diagnostic. The response set may include, for example, at least some of the following responses: oxygen saturation, heart rate, pupillary response, blood pressure, sweat production, sudomotor activity, and/or respiration.

The controller stores the diagnostic response data characterizing the autonomic physiological responses of the subject to the diagnostic stimulation, step 305. The diagnostic response data may be stored, for example, in controller memory, the patient database and/or the protocol database.

In illustrative embodiments of the invention, the diagnostic response data is retrieved from memory and/or the database by the controller, and is processed by the controller to identify the posture, hereinafter the "primary posture," wherein the physiological responses of the subject exhibit a least amount of dysfunction relative to their corresponding statistical norms, step 307.

To determine the posture of least dysfunction, each of the physiological responses in each posture may be assigned a score by the controller based on the amount of dysregulation indicated. For example, each physiological response may receive a score based on its deviation from its corresponding statistical norm (i.e., a further or closer distance from a normal value). The scores in each posture may be combined to form a total score for each posture that represents the overall amount of dysfunction. It is to be understood that a wide variety of algorithms may be used in determining the scores. For example, certain response scores may be weighted different from others, or ignored, for example, if the measured response is deemed inaccurate.

The statistical norms used in determining the amount of dysregulation for the various autonomic physiological responses are known in the art, and can be identified, for example, in available literature. The statistical norm may be based on, without limitation, the age, gender, size, patient history and/or other characteristics of the subject.

In addition to determining the "primary posture, wherein the physiological responses of the subject exhibit a least amount of dysfunction, a body posture of greatest dysfunction may also be determined by the controller to use as a baseline against which to measure the efficacy of the treatment regimen. In various embodiments, a side of least dysfunction may be determined. For example, while testing for the primary posture, or after determining the primary posture, sensory stimuli may be provided with respect to both the left cortex of the brain and the right cortex of the brain to identify whether the measured physiological response indicates an increased or decreased dysregulation. It should be understood by one skilled in the art, that many other combinations of stimuli, various monitoring windows, and examination order or operation may be employed.

In step 309, the controller evaluates diagnostic response data to identify the stimulus, hereinafter the "primary stimulus," with respect to which the physiological responses of the subject exhibit a change in the amount of dysfunction towards their corresponding statistical norms when the subject is in the primary posture. The diagnostic response data used in this step may have been gathered in steps 303 and 305. Alternatively, after determining the primary posture, the stimulus array may be used again by the controller while the subject is in the primary posture to acquire further diagnostic data.

In various embodiments, the primary stimulus may be the stimulus from the stimulus set that moves the autonomic metrics most efficiently toward its corresponding statistical norm. Furthermore, the stimulus may be fine-tuned to determine one or more stimulus parameter values that provide the most efficient physiological response by the subject. Illustratively, if auditory stimulation was determined to be the primary stimulus in the primary posture, the most efficient duration, amplitude, and/or frequency of the auditory stimulation may be determined. Other combinations of posture and stimulus require optimization of other parameters, as should be apparent to a person having ordinary skill in the art.

Once these processes 301-309 are complete, a treatment strategy may be determined and performed by the controller under the guidance of the healthcare practitioner, as described in more detail below. Such a strategy may be a function of a number of elements. As described above, these elements may include the primary posture and the primary stimulus and its associated parameters. Another element may be the collection of sensory modalities or stimulations which drive the vital centers toward normalized physiology or normal autonomic windows, as these adaptive competent stimulations are capable of producing adaptive neuroplasticity, and therefore promote system integrity and function. Other elements may be considered in determining the treatment strategy, if deemed relevant by the physician.

Figure 4:
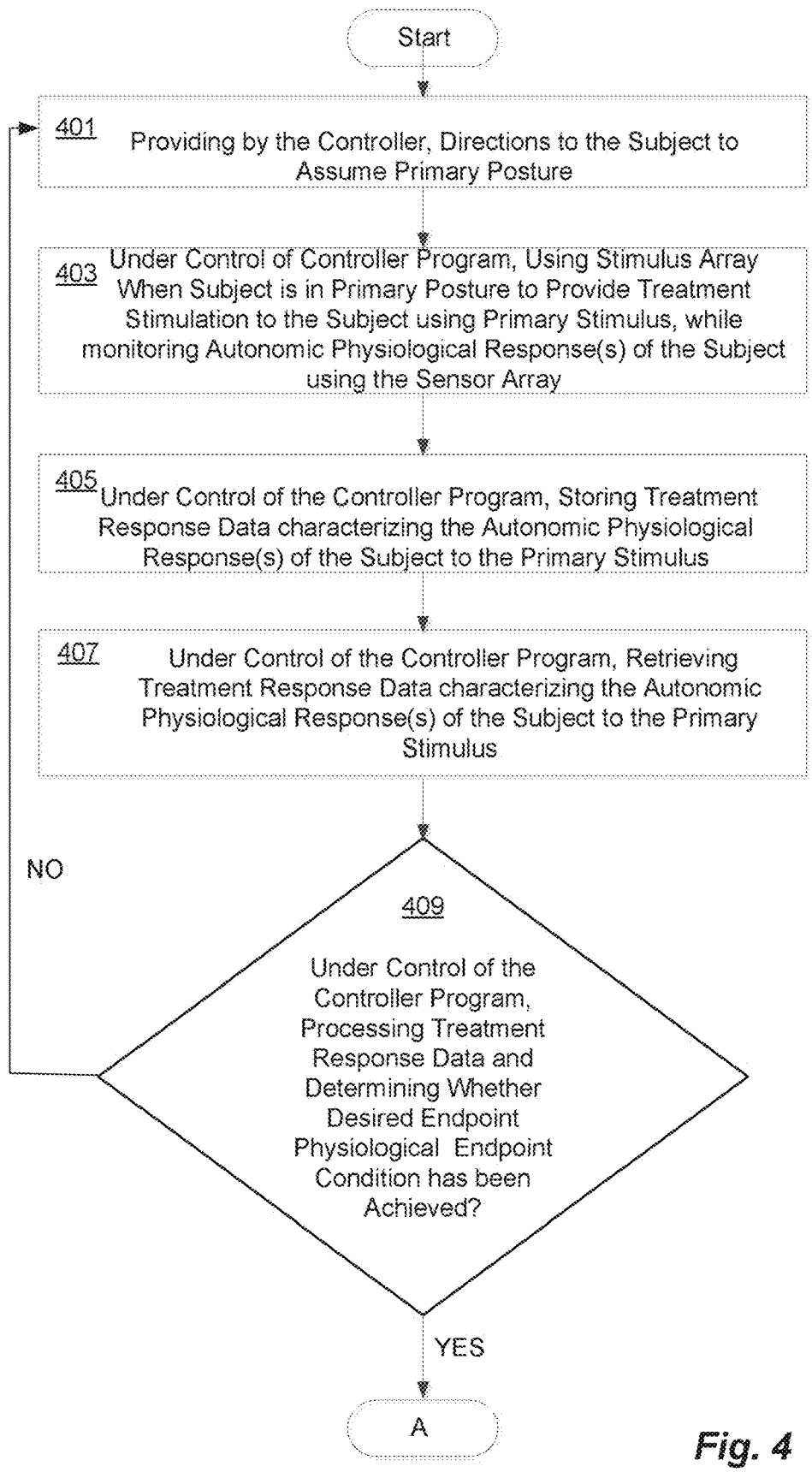
FIG. 4 shows a protocol for the treatment of a subject with acquired brain injury and dysfunction, in accordance with an embodiment of the invention.

FIG. 4 shows a protocol for the treatment of a subject with acquired brain injury and dysfunction, in accordance with various embodiments of the invention. To start, the controller, under control of the diagnostic and treatment program, provides instructions to the subject to assume the primary posture, step 401. Optionally, the controller may also instruct the subject to assume a side of least dysfunction while in the primary posture. For example, the subject may be instructed to lay down on his left or right side.

Although beginning the treatment at the posture of least dysfunction is unconventional and counter intuitive, it has been found to be most beneficial. Cortical Integrative Therapy (CIT), in accordance with embodiments of the invention, applies the principles of neuroplasticity which is predicated upon the knowledge that neuronal activity constantly changes the number and quality of the individual connections between neurons and in the case of catastrophic injury, e.g. stroke, large scale remapping of cortical connections can occur. Neuroplasticity at its core consists of two major processes; Long Term Potentiation and Long Term Depression. Long Term Potentiation (LTP) is the increase in number and strength of synaptic connections due to high frequency stimulation of the synapses. The increased number synapses occur through a multi-step process known as dendritic arborization. Long Term Depression (LTD) is the opposite of LTP in that it reduces the number and efficacy of synaptic connections due to low frequency stimulation and active pruning of the dendrites. This process contributes to an unlearning process which can allow for correction of errors in learned motor behaviors or forgetting traces of things we learned long ago. The excitatory neurotransmitter glutamate plays an important role in LTP and LTD regulation. Glutamate's receptors NMDA and AMPA can be overactivated by a "glutamatergic storm" causing an Excitotoxic reaction which occurs when glutamate concentration in the synapse cannot be decreased rapidly enough and/or reaches very high levels to cause death of the neuron (apoptosis). One of CIT's major goals during treatment is to prevent this excitotoxic reaction by the monitoring of the patients vital/autonomic nervous system responses so as to not exceed the patient's ability to handle the strain of the therapeutic stimulus on their body's systems.

Also, CIT's application and understanding of the role the vestibular system, by definition, takes into account how posture, movement, and the perception of posture and movement dictates a large portion of brain activity as well as directly modulating vital control centers. An example of this is that we sleep lying down, as opposed to standing, this posture lowers the amount of gravitational/vestibular input which decreases stimulation on systems like the hemodynamic-cardio-respiratory mechanisms that are responsive and regulated by changes in posture and movement. Clinical experience has shown that many orthostatic conditions or movement disorders respond with increased or decreased symptom expression depending on the patient's posture.

Thus, in illustrative embodiments of the invention, the posture of least dysfunction coupled with the optimal competent stimulus advantageously offers the greatest opportunity for the patient to improve/heal using the principles of neuroplasticity and the phenomenon of arborization of the remaining healthy neurons.

Referring back to FIG. 4, while the subject is in the primary posture, the controller uses the stimulus array to provide treatment stimulation to the subject by the primary stimulus, while using the sensor array to monitor the set of autonomic physiological responses of the subject to the treatment stimulation, step 403. The treatment response data characterizing the responses of the subject to the primary stimulation is stored, step 405.

Under control of the program, the treatment response data is retrieved by the controller, step 407, and processed to determine whether a desired endpoint physiological condition has been achieved by the subject for the primary posture and the primary stimulus, step 409. If so, the process may be terminated. Alternatively, the treatment may continue, for example, as described below with reference to FIG. 5.

The desired endpoint physiological condition may be, without limitation, that the physiological responses to the primary stimulus approach a state of normalcy relative to their corresponding statistical norms. The endpoint physiological condition may entail, for example, that the physiological responses are within their corresponding statistical norms, or a predefined amount from their corresponding statistical norms. If the desired endpoint physiological condition is not met, then, under control of the program, the steps 401, 403, 405 and 407 may be repeated until the endpoint physiological response is met.

At this point, by providing optimal stimulation at a posture of least dysfunction, a physical transformation occurs in the brain (i.e., thalamocortical pathways in the brain are promoted), without exceeding the patient's ability to handle the strain of the therapeutic stimulus on their body's systems. Furthermore, CIT utilizes neuro-physiological windows measurable in patients in diverse compromised and non-communicative states to elicit communication, pure and innate, to and from the Central Nervous System free of subjective misinterpretation from examiners and the suffering patients.

Figure 5:
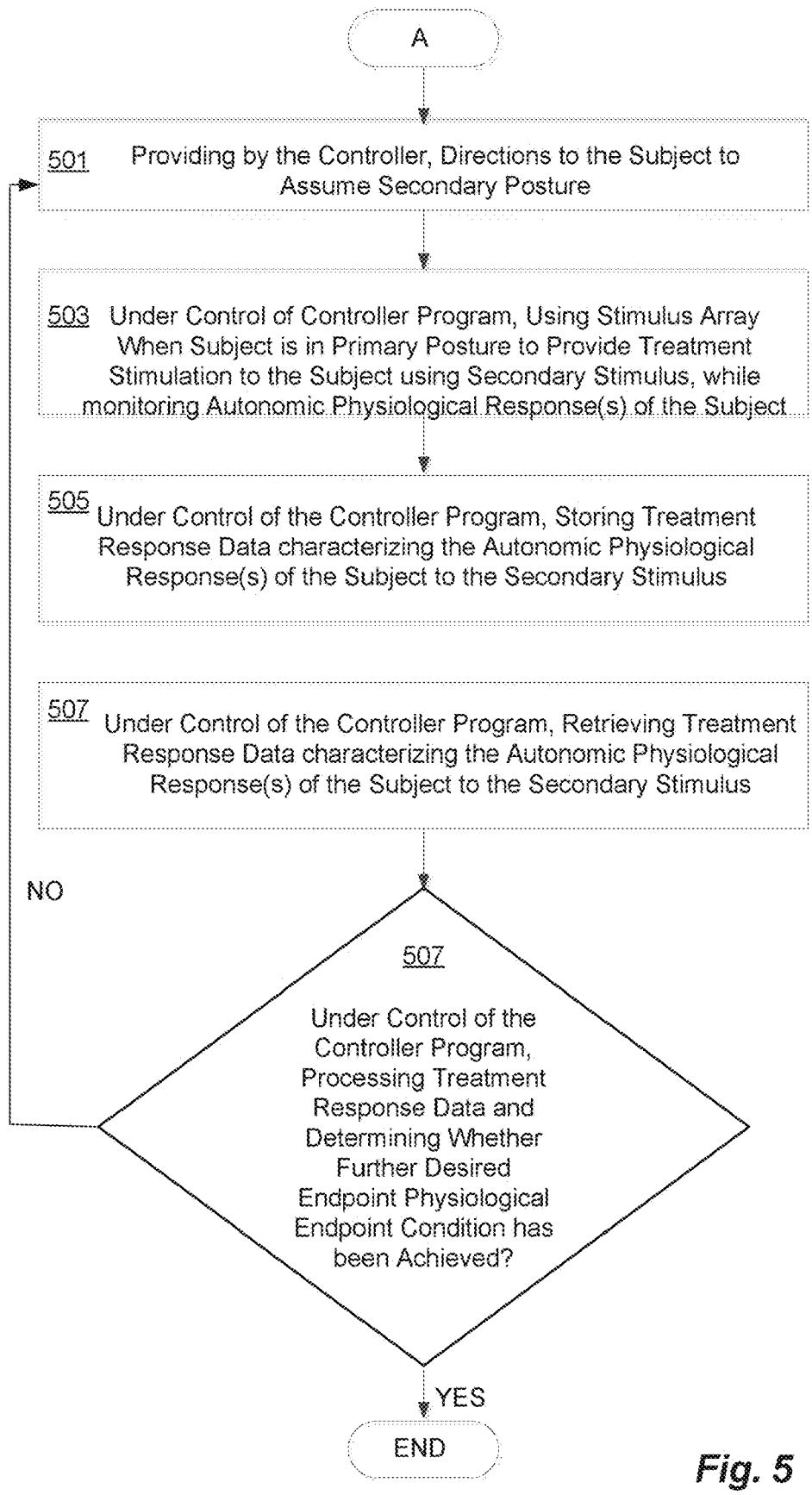
FIG. 5 shows a protocol for the further treatment of a subject with acquired brain injury and dysfunction, in accordance with an embodiment of the invention.

Upon the desired endpoint physiological condition associated with the primary posture and primary stimulus being met, treatment may continue further. FIG. 5 shows a protocol, performed by the controller under control of the controller program, for the further treatment of the subject, in accordance with an embodiment of the invention. The controller provides direction to the subject to assume a posture, hereinafter the "secondary posture," in the posture set other than the primary posture, step 501. The secondary posture may be determined, without limitation, using diagnostic processes similar to that used to determine the primary posture. For example, the controller may provide directions to the subject to sequentially assume postures different from the primary posture. In each of these postures, the stimulus array may then be used by the controller to provide to the subject sequentially each stimulus in a stimulus set (e.g., the stimulus set described above) so as to provide diagnostic stimulation. The controller stores the diagnostic response data characterizing the autonomic physiological responses of the subject to the diagnostic stimulation in each of the postures. The diagnostic response data is retrieved from memory and/or the database by the controller, and is processed by the controller to identify the secondary posture, wherein the physiological responses of the subject exhibit a least amount of dysfunction relative to their corresponding statistical norms.

While the subject is in the secondary posture, the stimulus array is used by the controller to provide treatment stimulation to the subject by a selected stimulus in the stimulus set, hereinafter the "secondary stimulus," step 503. The sensor array is used by the controller to monitor the set of autonomic physiological responses of the subject to the treatment stimulation in the secondary posture. The treatment response data characterizing the Autonomic Physiological Response(s) of the Subject to the Secondary Stimulus is stored by the controller, step 505.

To determine the secondary stimulus, the protocol may include further diagnostic processes. For example, and without limitation, these diagnostic processes may be similar to those performed in determining the primary stimulus. More particularly, the stimulus array may be used by the controller to provide to the subject sequentially each stimulus in the stimulus set while in the secondary posture so as to provide diagnostic stimulation. The sensor array is used by the controller to monitor the set of autonomic physiological responses of the subject to the diagnostic stimulation. The diagnostic response data characterizing the responses of the subject to such diagnostic stimulation is stored by the controller. The diagnostic response data may then be retrieved by the controller and processed to identify the secondary stimulus with respect to which the physiological responses of the subject exhibit a change in the amount of dysfunction towards their corresponding statistical norms when the subject is in the secondary posture.

Referring back to FIG. 5, the treatment response data characterizing the autonomic physiological responses of the subject to the secondary stimulus may then be retrieved by the controller, step 507. These autonomic physiological responses may then be processed by the controller to determine whether a further desired endpoint physiological endpoint is achieved, step 509. If so, the treatment process may be terminated or may be again repeated at a further posture and selected stimulus. If the further desired endpoint physiological condition is not met, then, under control of the program, the steps 501, 503, 505 and 507 may be repeated until the endpoint physiological response is met.

Similar to the desired endpoint physiological condition associated with the primary posture, the desired endpoint physiological condition associated with the secondary posture may be, without limitation, that the physiological responses to the secondary stimulus approach a state of normalcy relative to their corresponding statistical norms. By providing the secondary stimulation at the secondary posture and secondary stimulus, further physical transformation occurs in the brain, again without exceeding the patient's ability to handle the strain of the therapeutic stimulus on their body's systems.

Figure 6A:
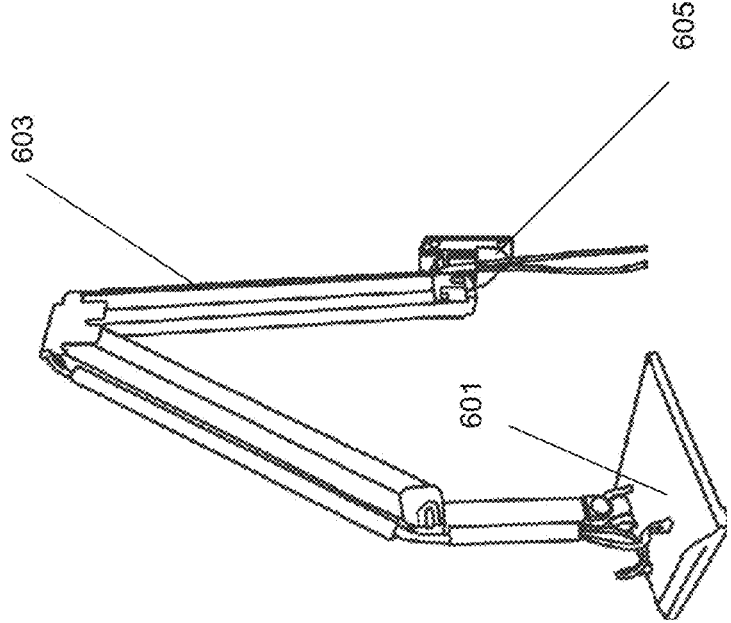
FIG. 6(*a*) shows a display coupled to an articulated swing-arm, in accordance with an embodiment of the invention.
Figure 6B:
Figure 6C:
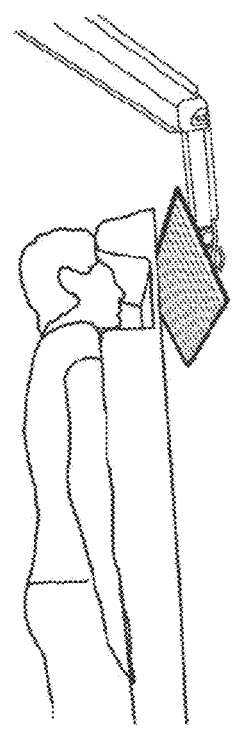

FIG. 6(*a*) shows a display 601 coupled to an articulated swing-arm 603, in accordance with an embodiment of the invention. The display 601 may be used, as described in above embodiments, as a user interface for either the subject or the health practitioner, or to provide stimulation to the subject. The swing-arm 603 may be attached to a wall, or may be integrated, for example, onto a wheeled stand. The articulated swing-arm 603 may resist the downward force generated by the display 601, and may be foldable towards the wall or wheeled stand to create a more compact footprint and/or allow greater portability (if on a wheeled stand). Additional articulations may allow for additional folding of the device to provide an even greater compact footprint. The display 601 and or swing-arm 603 may include locking mechanisms to secure their position in various degrees of the possible folded or unfolded configurations. The swing-arm 603 may be telescopic, and/or may slide through a clamping device on the wall or base that will allow the length that that swing-arm boom arm projects out from the wall or stand to be adjusted. Movement and position of the display 601 via the articulated swing-arm 603 may be controlled robotically via the controller. The display 601 may be coupled to a surge protector, and/or a battery back-up may be incorporated.

The display 601 may be adjustable in multiple ways. For example, the elevation, angle, lateral position and/or distance from the subject's face may be adjusted to obtain the desired relative position for the needed stimulation/testing procedure. This allows for treatment or testing to occur with the patient in a variety of positions, which may include; lying, reclined sitting, upright sitting, standing, marching-in-place, walking on a treadmill, vibration platform, computer dynamic posturography, or other sensory-motor activity. FIG. 6(*b*) shows a subject 607 using the display 601 in a standing position, while FIG. 6(*c*) shows the subject 607 in a prone position using the display 601, in accordance with various embodiments of the invention.

While the controller-based apparatus may advantageously perform the above-described protocol with minimal supervision by the health practitioner, the health practitioner may nevertheless have the capability to monitor or supervise controller activity to the extent desired. Furthermore, the health practitioner may simultaneously or consecutively provide an additional therapeutic regime to the subject to promote better healing.

Figure 7:
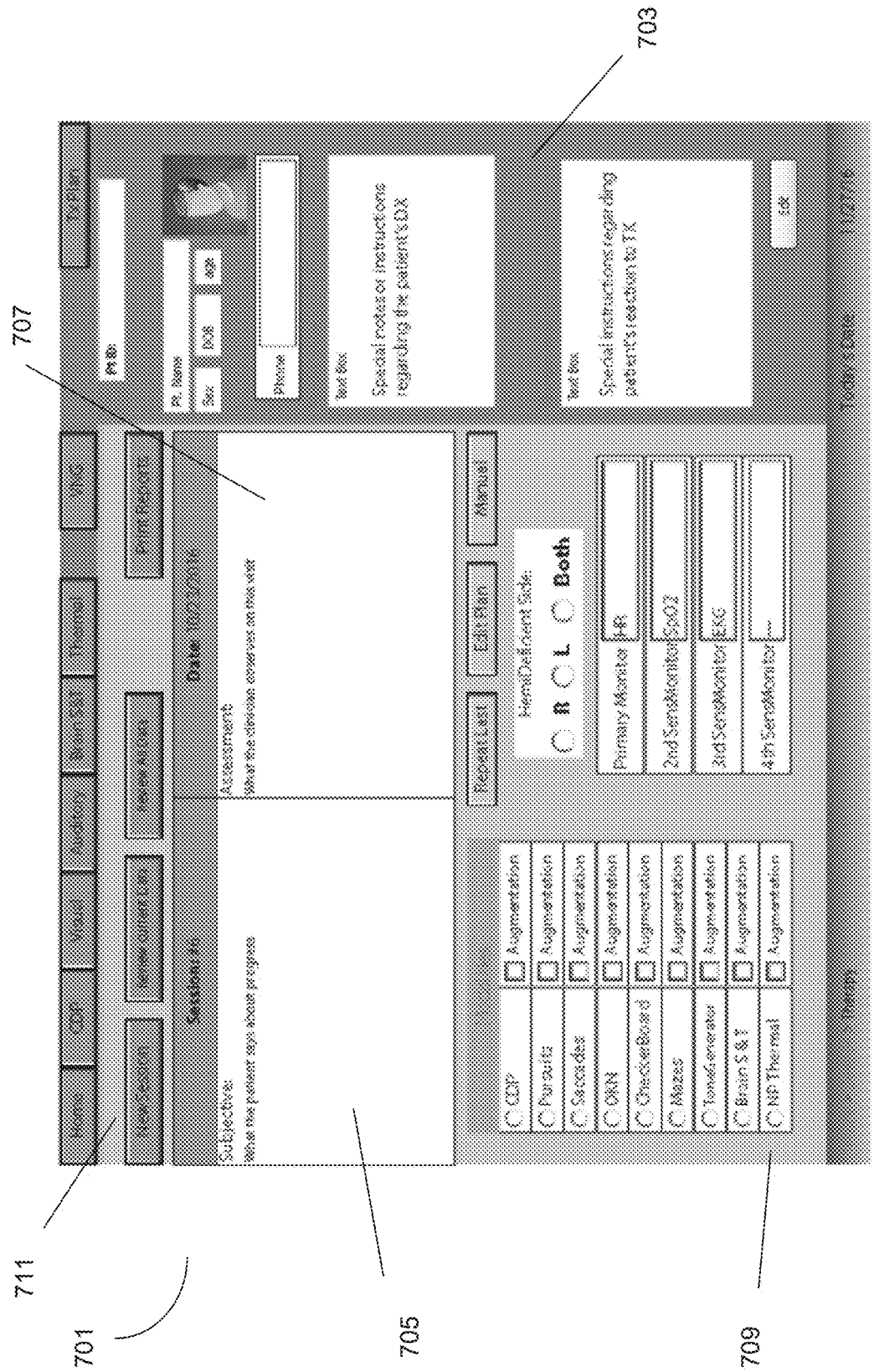
FIG. 7 is an exemplary screen shot that may be provided by the controller to a health practitioner, in accordance with an embodiment of the invention.
Figure 8:
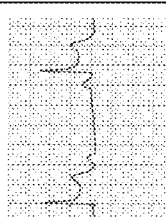
FIG. 8 is a screen shot showing sensor data that may be provided by the controller to a health practitioner, in accordance with an embodiment of the invention.

Illustratively, FIG. 7 is an exemplary screen shot that may be provided to a health practitioner by the controller, in accordance with an embodiment of the invention. On the right side of the screen is an area 703 in which the health practitioner may enter and/or retrieve information regarding the subject. The screen also includes an area 705 in which subjective notes of the patient for a particular visit can be entered or reviewed, and an area 707 in which the health practitioner can enter or review their own assessments of the visit. The bottom left area of the screen 709 shows particular information regarding the diagnostics/treatment being performed. At the top of the screen 711 is a menu for the various diagnostics/treatments, sessions, data, and printouts that may be selected via, without limitation, a touch panel, or a point/click device. FIG. 8 is a screen shot showing sensor data that may be provided by the controller to a health practitioner, in accordance with an embodiment of the invention.

A conceptual framework for rehabilitation in accordance with the controller and methods described herein may be found in the emergent concept of Dr. Antonio Damasio's brain-body maps. See, for example: Damasio, Antonio R. *Looking for Spinoza: Joy, Sorrow, and the Feeling Brain* (Harcourt, 2003); Damasio, Antonio R. *Descartes' Error: Emotion, Reason, and the Human Brain* (Penguin, 2005); and Damasio, Antonio R. et al., "Minding the Body". *Daedalus* 135.3 (2006): 15-22. Another possible framework is provided by Dr. Rodolfo Llinás and his brain timing mechanisms. See, for example: Llinás, Rodolfo et al., *The Mind-Brain Continuum: Sensory Processes* (Bradford Books, 1996); Llinás, Rodolfo (1998). "The neuronal basis for consciousness". Phil. Tran. R. Soc. Lond. (The Royal Society) 353: 1841-1849; Llinas, Rodolfo (1999). "Thalamocortical dysrhythmia: a neurological and neuropsychiatric syndrome characterized by magnetoencephalography". PNAS 96 (26): 15222-15227; Llinás, Rodolfo R. *I of the Vortex: From Neurons to Self* (MIT Press, 2001); Llinás, Rodolfo (2002). "Temporal binding via coincidence detection of specific and nonspecific thalamocortical inputs: A voltage-dependent dye-imaging study in mouse brain slices". PNAS (The National Academy of Sciences) 99 (1): 449-454; see also Jones, Edward G. "Thalamocortical dysrhythmia and chronic pain". *Pain* (Elsevier) 150: 4-5. 2010 and citations therein. Understanding of the phenomenon of coherence may also inform understanding of the underlying mechanisms. The articles cited in this paragraph are incorporated by reference as if set forth in their entirety herein.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A controller-based apparatus, for diagnosis and treatment of a subject with acquired brain injury, by stimulation of afferent fibers so as indirectly to cause improvement in the area of the brain affected by the injury, and in overall brain function, the apparatus comprising:

a controller, the controller configured to execute a diagnostic and treatment program, that performs a protocol for the diagnosis and the treatment, the program operating under guidance of a health practitioner;

a display, coupled to the controller, configured by the program to provide data to the health practitioner concerning performance of the subject under the protocol as well as a user interface for the health practitioner to operate the diagnostic and treatment program;

a stimulus array, coupled to the controller, configured to provide stimulation to the subject, the stimulation being provided from a stimulus set selected from the group consisting of TENS, non-painful heat, non-painful cold, visual, occulo-motor stimulation, crude touch, olfactory stimulation, vestibular stimulation, auditory stimulation and combinations thereof;

a sensor array, coupled to the controller, configured to monitor a response set of autonomic physiological responses of the subject, to such stimulation, the response set selected from the group consisting of oxygen saturation, heart rate, pupillary response, blood pressure, sweat production, sudomotor activity, and respiration;

(a) wherein the protocol includes diagnostic processes comprising:

providing by the controller, under control of the program, directions to the subject to assume sequentially a plurality of distinct postures in a posture set selected from the group consisting of walking, standing, sitting, prone and supine;

while the subject is in each of the selected postures, using the stimulus array, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation;

storing, under control of the program, diagnostic response data characterizing the responses of the subject to such diagnostic stimulation;

retrieving, under control of the program, the diagnostic response data;

processing, under control of the program, the diagnostic response data to identify the posture, hereinafter the "primary posture," wherein the physiological responses of the subject exhibit a least amount of dysfunction relative to their corresponding statistical norms;

processing, under control of the program, the diagnostic response data identifying the stimulus, hereinafter the "primary stimulus," with respect to which the physiological responses of the subject exhibit a change in the amount of dysfunction towards their corresponding statistical norms when the subject is in the primary posture; and (b) wherein the protocol includes treatment processes comprising:

(i) providing by the controller, under control of the program, direction to the subject to assume the primary posture;

(ii) while the subject is in the primary posture, using the stimulus array, under control of the program, to provide treatment stimulation to the subject by the primary stimulus in the stimulus set while using the sensor array, under control of the program, to monitor the set of autonomic physiological responses of the subject to the treatment stimulation;

(iii) storing, under control of the program, treatment response data characterizing the responses of the subject to the treatment stimulation; and (iv) under control of the program, retrieving and processing the treatment response data to determine if the treatment response data show achievement by the subject of a desired endpoint physiological condition, for the primary posture and the primary stimulus, in which the physiological responses to the identified stimulus approach a state of normalcy relative to their corresponding statistical norms and if not, then, under control of the program, repeating processes (i), (ii), (iii), and (iv);

wherein the protocol promotes thalamocortical pathways within the brain.

2. The controller-based apparatus, according to claim 1, wherein the protocol includes treatment processes further comprising:

if the treatment response data show achievement by the subject of a desired endpoint physiological condition, for the primary posture and the primary stimulus, then under control of the program, (v) providing by the controller, under control of the program, direction to the subject to assume a posture, hereinafter the "secondary posture," in the posture set other than the primary posture;

(vi) while the subject is in the secondary posture, using the stimulus array, under control of the program, to provide treatment stimulation to the subject by a selected stimulus in the stimulus set, hereinafter the "secondary stimulus," while using the sensor array, under control of the program, to monitor the set of autonomic physiological responses of the subject to the treatment stimulation in the secondary posture;

(vii) storing, under control of the program, secondary posture treatment response data characterizing the responses of the subject to the treatment stimulation in the secondary posture;

(viii) under control of the program, retrieving and processing the secondary posture treatment response data to determine if the secondary posture treatment response data show a further desired endpoint physiological condition is achieved in which the physiological responses to the secondary stimulus at the secondary posture approach a state of normalcy relative to a their corresponding statistical norms; and (ix) if not, then, under control of the program, repeating processes (v), (vi), (vii), and (viii), and otherwise terminating the treatment process.

3. The controller-based apparatus according to claim 2, wherein the protocol further includes diagnostic processes comprising:

while the subject is in the secondary posture,
using the stimulus array, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation;

storing, under control of the program, diagnostic response data characterizing the responses of the subject to such diagnostic stimulation;

retrieving, under control of the program, the diagnostic response data;

processing, under control of the program, the diagnostic response data identifying the secondary stimulus with respect to which the physiological responses of the subject exhibit a change in the amount of dysfunction towards their corresponding statistical norms when the subject is in the secondary posture.

4. The controller-based apparatus according to claim 1, wherein the acquired brain injury includes post-concussion syndrome (PCS).

5. The controller-based apparatus according to claim 4, wherein the acquired brain injury is associated with at least one symptom selected from the group consisting of headaches, dizziness, neck pain, stiff neck, nervousness, fatigue, irritability, cold sweats, excessive eye sensitivity to light and combinations thereof, and wherein the protocol results in a decrease in the at least one symptom.

6. The controller-based apparatus according to claim 1, wherein the display is coupled to an articulated swing-arm.

7. The controller-based apparatus according to claim 6, where the controller, under control of the program, controls the articulated swing-arm to assume various positions and/or orientations.

8. The controller-based apparatus according to claim 1, further including a speaker, a microphone and/or a headphone, functionally coupled to the controller.

9. The controller-based apparatus according to claim 1, further including a video headset configured to be worn by the subject, and wherein the controller, under control of the program, provides and/or receives visual information to and/or from the subject via the video headset, respectively.

10. A non-transitory storage medium, encoded with instructions for a diagnostic and treatment program, which when executed on a system having a controller, a display, a stimulus array, and a sensor array, establishes processes for performing a protocol for the diagnosis and the treatment of a subject with acquired brain injury, by stimulation of afferent fibers so as indirectly to cause improvement in the area of the brain affected by the injury, and in overall brain function, the program operating under guidance of a health practitioner; wherein:

the display is coupled to the controller and configured by the program to provide data to the health practitioner concerning performance of the subject under the protocol as well as a user interface for the health practitioner to operate the diagnostic and treatment program;

the stimulus array is coupled to the controller and configured to provide stimulation to the subject, the stimulation being provided from a stimulus set selected from the group consisting of TENS, non-painful heat, non-painful cold, visual, occulo-motor stimulation, crude touch, olfactory stimulation, vestibular stimulation, auditory stimulation and combinations thereof; and the sensor array is coupled to the controller and configured to monitor a response set of autonomic physiological responses of the subject, to such stimulation, the response set selected from the group consisting of oxygen saturation, heart rate, pupillary response, blood pressure, sweat production, sudomotor activity, and respiration;

(a) wherein the protocol includes diagnostic processes comprising:

providing by the controller, under control of the program, directions to the subject to assume sequentially a plurality of distinct postures in a posture set selected from the group consisting of walking, standing, sitting, prone and supine;

while the subject is in each of the selected postures,
using the stimulus array, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation;

storing, under control of the program, diagnostic response data characterizing the responses of the subject to such diagnostic stimulation;

retrieving, under control of the program, the diagnostic response data;

processing, under control of the program, the diagnostic response data to identify the posture, hereinafter the "primary posture," wherein the physiological responses of the subject exhibit a least amount of dysfunction relative to their corresponding statistical norms;

processing, under control of the program, the diagnostic response data identifying the stimulus, hereinafter the "primary stimulus," with respect to which the physiological responses of the subject exhibit a change in the amount of dysfunction towards their corresponding statistical norms when the subject is in the primary posture; and (b) wherein the protocol includes treatment processes comprising:
  (i) providing by the controller, under control of the program, direction to the subject to assume the primary posture;
  (ii) while the subject is in the primary posture, using the stimulus array, under control of the program, to provide treatment stimulation to the subject by the primary stimulus in the stimulus set while using the sensor array, under control of the program, to monitor the set of autonomic physiological responses of the subject to the treatment stimulation;
  (iii) storing, under control of the program, treatment response data characterizing the responses of the subject to the treatment stimulation; and
  (iv) under control of the program, retrieving and processing the treatment response data to determine if the treatment response data show achievement by the subject of a desired endpoint physiological condition, for the primary posture and the primary stimulus, in which the physiological responses to the identified stimulus approach a state of normalcy relative to their corresponding statistical norms and if not, then, under control of the program, repeating processes (i), (ii), (iii), and (iv);

wherein the protocol promotes thalamocortical pathways within the brain.

11. The non-transitory storage medium according to claim 10, wherein the protocol includes treatment processes further comprising:
if the treatment response data show achievement by the subject of a desired endpoint physiological condition, for the primary posture and the primary stimulus, then under control of the program,
  (v) providing by the controller, under control of the program, direction to the subject to assume a posture, hereinafter the "secondary posture," in the posture set other than the primary posture;
  (vi) while the subject is in the secondary posture, using the stimulus array, under control of the program, to provide treatment stimulation to the subject by a selected stimulus in the stimulus set, hereinafter the "secondary stimulus," while using the sensor array, under control of the program, to monitor the set of autonomic physiological responses of the subject to the treatment stimulation in the secondary posture;
  (vii) storing, under control of the program, secondary posture treatment response data characterizing the responses of the subject to the treatment stimulation in the secondary posture;
  (viii) under control of the program, retrieving and processing the secondary posture treatment response data to determine if the secondary posture treatment response data show a further desired endpoint physiological condition is achieved in which the physiological responses to the secondary stimulus at the secondary posture approach a state of normalcy relative to a their corresponding statistical norms; and
  (ix) if not, then, under control of the program, repeating processes (v), (vi), (vii), and (viii), and otherwise terminating the treatment process.

12. The non-transitory storage medium according to claim 11, wherein the protocol further includes diagnostic processes comprising:
while the subject is in the secondary posture,
  using the stimulus array, under control of the program, to provide to the subject sequentially each stimulus in the stimulus set so as to provide diagnostic stimulation, while using the sensor array, under control of the program, to monitor the set of autonomic physiological responses of the subject to the diagnostic stimulation;
  storing, under control of the program, diagnostic response data characterizing the responses of the subject to such diagnostic stimulation;
  retrieving, under control of the program, the diagnostic response data;
  processing, under control of the program, the diagnostic response data identifying the secondary stimulus with respect to which the physiological responses of the subject exhibit a change in the amount of dysfunction towards their corresponding statistical norms when the subject is in the secondary posture.

13. The non-transitory storage medium according to claim 10, wherein the acquired brain injury includes post-concussion syndrome (PCS).

14. The non-transitory storage medium according to claim 10, wherein the acquired brain injury is associated with at least one symptom selected from the group consisting of headaches, dizziness, neck pain, stiff neck, nervousness, fatigue, irritability, cold sweats, excessive eye sensitivity to light and combinations thereof, and wherein the protocol results in a decrease in the at least one symptom.

15. The non-transitory storage medium according to claim 10, wherein the system further including a video headset configured to be worn by the subject, and wherein the controller, under control of the program, provides and/or receives visual information to and/or from the subject via the video headset, respectively.

* * * * *